United States Patent [19]
Clawson et al.

[11] Patent Number: 5,392,770
[45] Date of Patent: Feb. 28, 1995

[54] TUBING CIRCUIT SYSTEMS FOR HUMIDIFIED RESPIRATORY GAS

[76] Inventors: Burrell E. Clawson, 2425 Sunset Dr.; James Weigl, 18815 Hermosa St., both of Riverside, Calif. 92506

[21] Appl. No.: 85,315

[22] Filed: Jun. 29, 1993

[51] Int. Cl.6 .......................................... A61M 16/00
[52] U.S. Cl. .............. 128/203.77; 128/204.17; 128/912; A61M/16/00
[58] Field of Search ................ 128/204.18, 204.17, 128/203.12, 203.16, 203.17, 204.21, 207.19, 202.22, 911, 912, 203.27

[56] References Cited

U.S. PATENT DOCUMENTS

| | | | |
|---|---|---|---|
| 1,163,657 | 12/1915 | Hadaway, Jr. | 392/403 |
| 3,820,540 | 6/1974 | Hirtz et al. | 128/203.27 |
| 3,873,806 | 3/1975 | Schossow | 392/402 |
| 3,903,883 | 9/1975 | Pecina et al. | 128/200.21 |
| 4,007,737 | 1/1977 | Paluch | 128/201.3 |
| 4,051,205 | 9/1977 | Grant | 261/70 |
| 4,108,953 | 8/1978 | Rocco | 261/142 |
| 4,192,836 | 3/1980 | Bartscher et al. | 261/142 |
| 4,201,204 | 5/1980 | Rinne et al. | 128/203.27 |
| 4,225,542 | 9/1980 | Wall et al. | 261/142 |
| 4,564,748 | 1/1986 | Gupton | 219/497 |
| 4,567,353 | 1/1986 | Aiba | 219/501 |
| 4,593,670 | 6/1986 | Nara et al. | 123/545 |
| 4,618,462 | 10/1986 | Fisher | 261/130 |
| 4,652,408 | 3/1987 | Montgomery | 261/130 |
| 4,676,237 | 6/1987 | Wood et al. | 128/203.17 |
| 4,682,010 | 7/1987 | Drapeau et al. | 219/381 |
| 4,708,831 | 11/1987 | Elsworth et al. | 261/130 |
| 4,753,758 | 6/1988 | Miller | 261/139 |
| 4,910,384 | 3/1990 | Silver | 392/396 |
| 4,967,744 | 11/1990 | Chua | 128/204.18 |
| 5,062,145 | 10/1991 | Zwaan et al. | 392/396 |
| 5,284,160 | 2/1994 | Dryden | 128/203.12 |

FOREIGN PATENT DOCUMENTS

| | | | |
|---|---|---|---|
| 1223930 | 3/1971 | European Pat. Off. | |
| 2250542 | 6/1975 | France | |
| 2173274 | 10/1986 | United Kingdom | 128/204.17 |
| 8602566 | 5/1986 | WIPO | 128/204.17 |

Primary Examiner—Edgar S. Burr
Assistant Examiner—Eric P. Raciti
Attorney, Agent, or Firm—Frank J. Uxa, Jr.; Gordon L. Peterson

[57] ABSTRACT

Tubing circuits systems for delivering humidified respiratory gas to a human or an animal are disclosed. The circuit systems include an inspiratory tubing segment and an expiratory tubing segment joined by a manifold assembly. The inspiratory tubing segment is coupled to a humidifier while the expiratory system is coupled to a conventional ventilator. A single heating element is positioned in both the inspiratory and expiratory tubing segment elements. Temperature sensing elements are located at or near the outlet of the inspiratory tubing segment and at or near the inlet of the inspiratory tubing segment. Preferably, portions of all of the single heating element, and the temperature sensors are held by a single connector. The system is very effective in use, safe and easy to use, and provides a convenient, straight forward and reliable system useful in monitoring and controlling the temperature of respiratory gases being delivered to a patient.

20 Claims, 3 Drawing Sheets

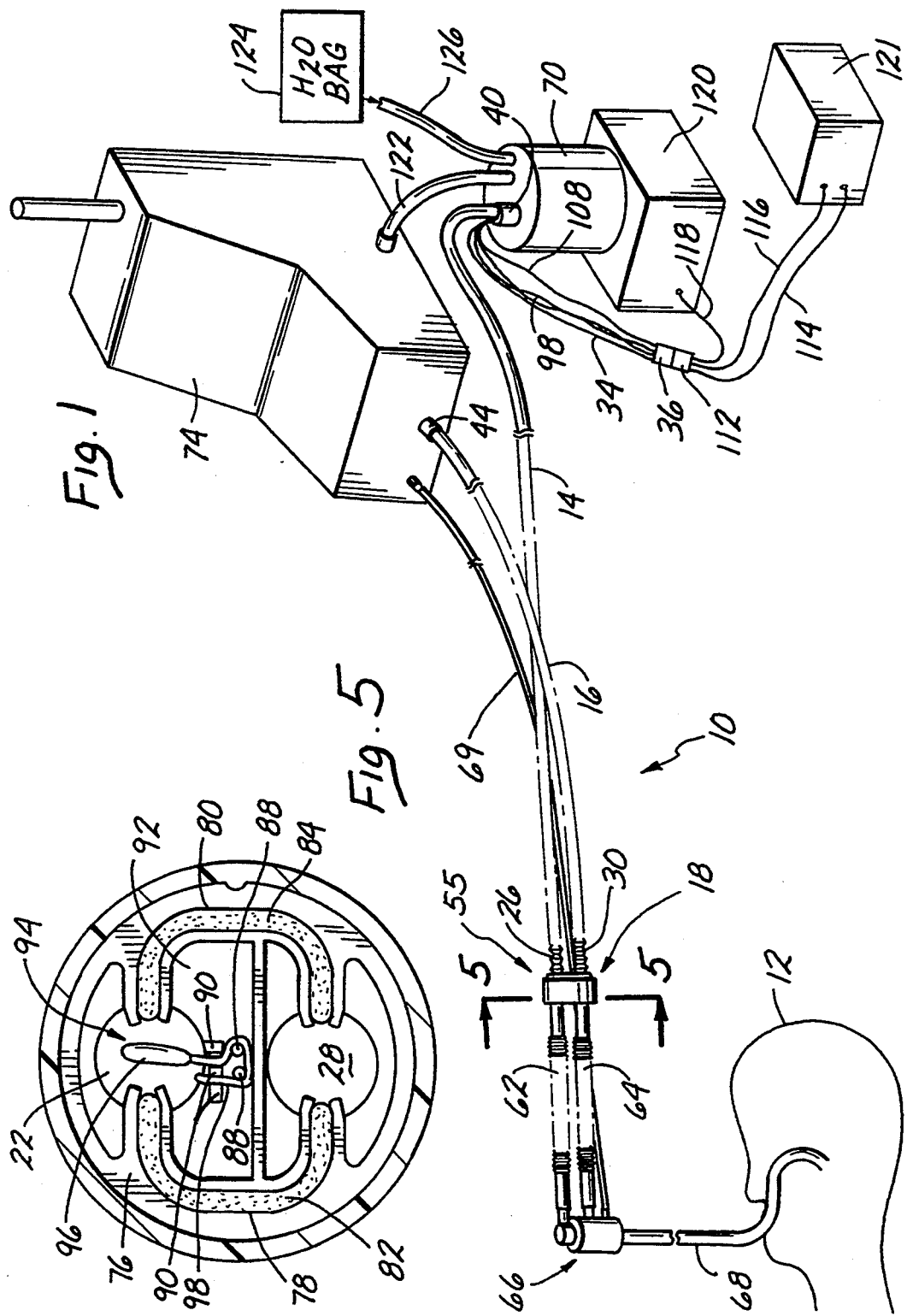

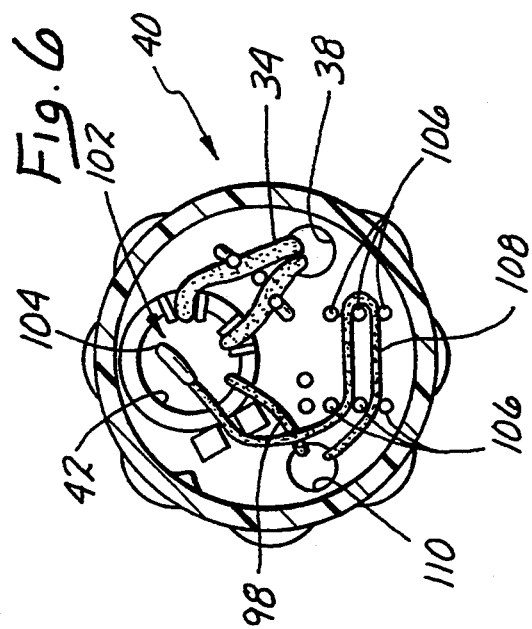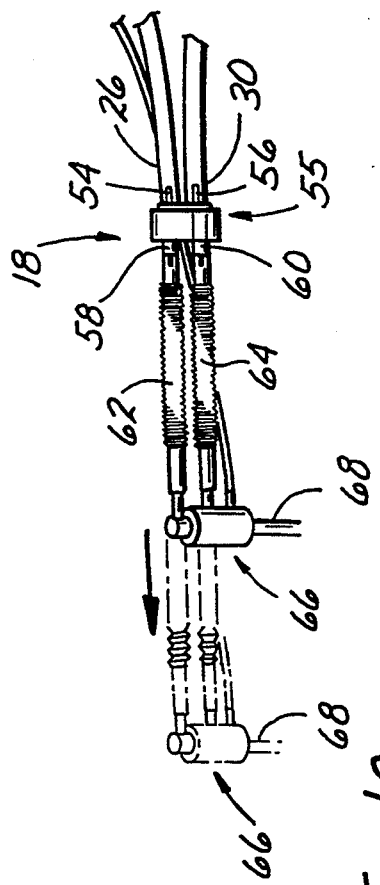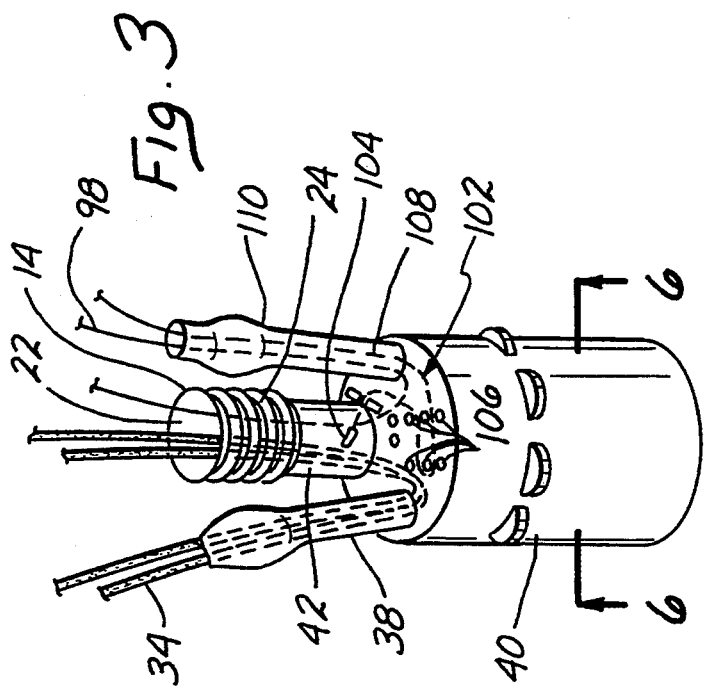

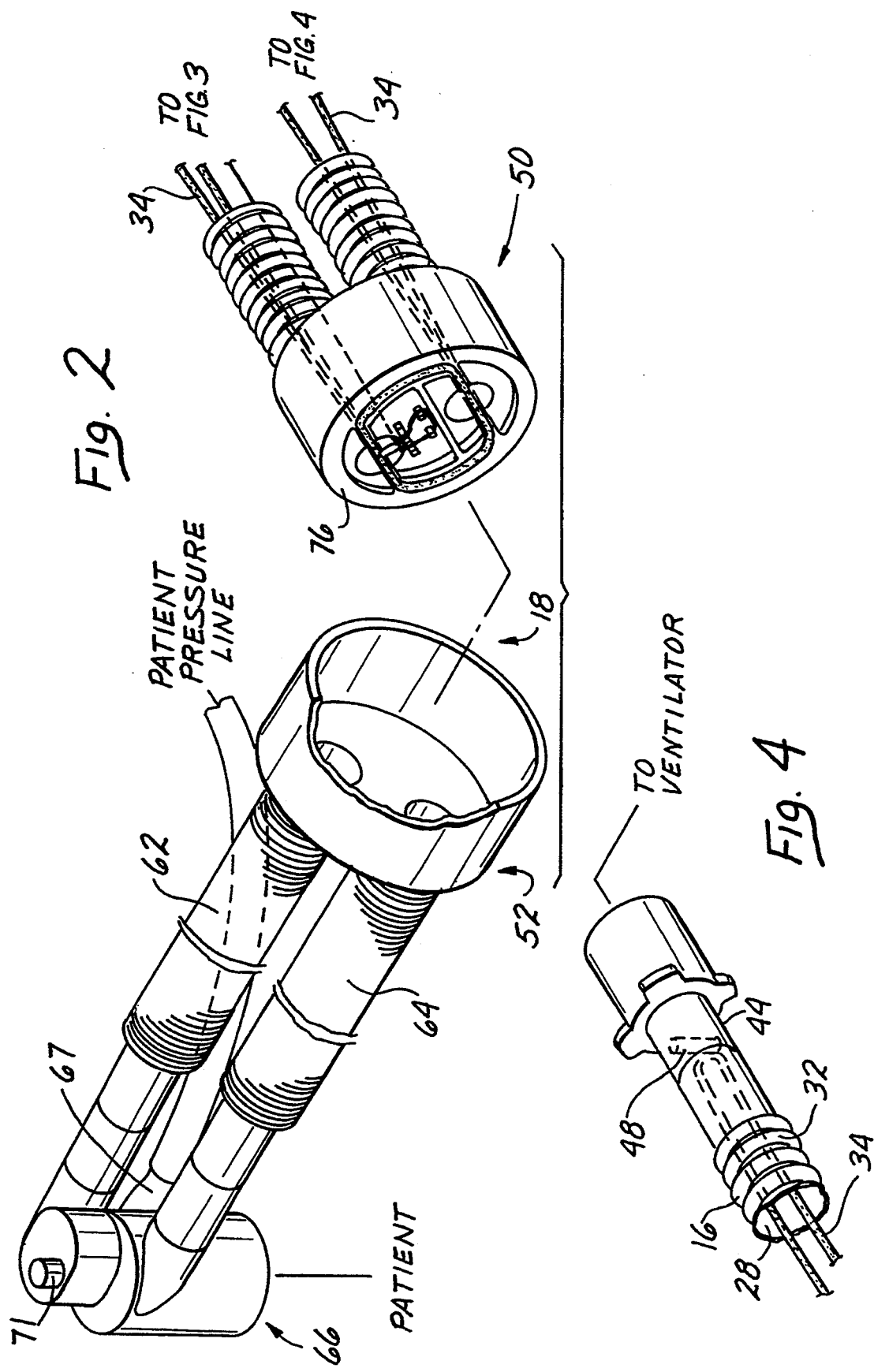

TUBING CIRCUIT SYSTEMS FOR HUMIDIFIED RESPIRATORY GAS

BACKGROUND OF THE INVENTION

The present invention relates to tubing circuit systems for delivering humidified respiratory gas to a human or an animal. More particularly, the invention relates to such tubing circuit systems which are straight forward in design and construction, and very effectively and reliably monitor and/or control the temperature of the humidified respiratory gas delivered to the human or animal, even under adverse or abnormal conditions.

Ventilators, with a humidifier typically at the outlet of the ventilator, supplying gas mixtures of air and one or more gaseous components, for example, oxygen, anesthesia and the like, to patients, usually in hospitals, do so through what is known as a "patient circuit". Such patient circuits conduct the gases out to a patient manifold and back to the ventilator's exhalation valve which closes and opens, raising and lowering the pressure to the patient's lungs in the typical ventilator arrangement.

Additionally, the patient circuits often have either water traps to collect condensate from the humidifiers in the inspiratory and expiratory flow tubes or they have heating wires in or around the tubes to minimize the condensation. When the circuit is heated, temperature sensors are included and are coupled to controllers to control the amount of heat provided to the patient circuit, and the humidifier's patient temperature probe, which is normally at the patient manifold, is moved back to the outlet of the humidifier. Most circuits also include a patient pressure sensing line connected to a port on or near the patient manifold. Sometimes other gas sampling and atomized drug treatment and suctioning ports exist for specialized occasional measurements or treatments.

Although heated patient circuits eliminate the need for water traps in the tubing legs, the prior art heated circuits do have certain problems and disadvantages. For example, because of the structure and/or location or placement of the temperature sensors in the prior art circuits, there is a relatively high propensity for such circuits to deliver respiratory gas which is either warmer (over temperature) or cooler (under temperature) than desired. Such warmer or cooler respiratory gas can result in patient discomfort and irritation, and even in severe respiratory system damage, particularly when the patient is a human infant or child, for example, under one year of age. In addition, these prior art heated patient circuits are relatively "unforgiving" of user or operator errors. For example, serious over temperatures or under temperatures are quite likely to occur if such prior art circuits are accidentally used backward, that is with the inspiratory line used as the expiratory line, and vice versa. Of course, it would be advantageous to provide a circuit system which reduces the severity, or even overcomes, one or more of these problems or concerns.

Elsworth et al U.S. Pat. No. 4,708,831 discloses a humidifier and circuit for delivery of humidified gases to a patient. Thermistors are provided in the inspiratory line and provide signals externally of the circuit to a control system. Also, two separate heating elements are provided, one in the inspiratory line and another in the expiratory line. Only the heating element in the inspiratory line is controlled by the control system. The systems disclosed in this patent are subject to temperature sensing errors, for example, because of heat losses due to the temperature signals being transported outside of the circuit. Also, slight reverse gas flows and/or convection currents can result in gas at a higher than desired, or even uncontrolled, temperature, (for example, from the expiratory line) being passed to the patient.

Systems which employ conventional external temperature probes are also susceptible to temperature sensing errors. For example, such probes can be sensitive to the temperature of the environment external to the circuit system, such as in an incubator (or at an incubator wall) and/or under a warmer, rather than accurately sensing the temperature of the gas in the circuit system.

French Patent No. 2,250,042 discloses a temperature detector at the end of a tubular humidifier heater. However, since the detector is located at one end of the heater, zero gas flow and convection currents can affect the reading of the detector, and small negative or reverse flows can inactivate the detector. Also, this French Patent concerns a humidifier, and not a heated patient circuit.

It would be advantageous to provide tubing circuit systems for delivery of humidified respiratory gas in which gas heating can be conveniently and reliably maintained, even under adverse or abnormal conditions, and/or in which temperatures can be accurately and reliably sensed and controlled.

SUMMARY OF THE INVENTION

New tubing circuit systems for delivering humidified respiratory gas to a human or animal have been discovered. The present systems are relatively straight forward in design and construction, are easy to use, and are reliable and "user forgiving" in use. The adverse consequences of user or operator errors are eliminated or at least significantly reduced in severity. For example, very few, if any, adverse consequences result if the present systems are inadvertently hooked up backwards, that is with the inspiratory line being used as the expiratory line and vice versa. Also, effects on the circuit system, for example, resulting in inaccurate temperature measurements, of the external environment are eliminated or reduced to insignificant levels. Temperature changes of the gas in the present tubing circuit systems due to the temperature of the external environment are eliminated or reduced to insignificant levels. In addition, the present tubing circuit systems eliminate: the need for sophisticated, touchy, multiple temperature probes, the accuracy of which is flow sensitive in many environments; user or operator errors in physical insertion of and use of such temperature probes; the need for microprocessor-based power controllers with elaborate logic; damage to temperature probes caused by using excessive force on wires or probe tip sheaths or caused by repeated sterilizations; over temperatures after suctioning and equipment change procedures which cause interruptions in gas flow through the circuit; unnecessary alarms because of over temperatures; and long term temperature probe damage and/or gradual calibration changes.

The temperature sensor assemblies associated with the present circuit systems are preferably disposable and, therefore, are used on a one-time basis. Moreover, the need for a separate temperature sensor and temperature controller for the heating wire associated with the expiratory line is eliminated. Further, using the present systems results in the time delay (or response time) between a temperature change and the time when the temperature sensor detects such temperature change preferably being reduced, more preferably minimized to the extent possible. Also, temperature errors are reduced, or minimized, even when the user or operator hooks up the present circuit backwards.

The present systems have applicability in high frequency ventilation since such systems employ high amplitude pulses (low flow damping) of the gas stream in these types of ventilators. Other possible applications include constant positive airway pressure (CPAP) systems. Also, adult patients when being weaned off of ventilators use low flows from constant pressure airway pressure systems and can benefit from the present tubing circuit systems. Further, anaesthesia circuits which use low flows can benefit from the present systems which retain or maintain gas temperatures at desired levels even when operating room temperatures are kept below 70° F. The present circuit systems can be sized and structured for use in infant, pediatric or adult applications.

The present tubing circuit systems provide for patient safety from over or under temperature gas; for relief from alarms which are very distressing to poor health patients; for patient safety if the user or operator hooks up the circuit backwards; and for minimum flow restriction.

In one broad aspect of the present invention, tubing circuit systems for delivering humidified respiratory gas to a human or animal are provided. Such systems comprise a first tubing segment (the inspiratory tube or line), a second tubing segment (the expiratory tube or line), and a manifold assembly. The inspiratory tube defines a first elongate hollow space, has an inlet for receiving humidified respiratory gas for passage through this hollow space toward the human or animal, and an outlet. The expiratory tube defines a second elongate hollow space and has an inlet for receiving exhaled gas from the human or animal and humidified respiratory gas for passage through this elongate hollow space away from the human or animal, and an outlet adapted to be joined to a ventilator to provide fluid communication between the second elongate hollow space and the ventilator. The manifold assembly includes a first port coupled to the expiratory tube, and a second port coupled to the expiratory tube.

In one embodiment, a heating element is positioned in the first elongate hollow space and the second elongate hollow space and is adapted to provide heat to the humidified respiratory gas passing through the first elongate hollow space and to the exhaled gas and humidified respiratory gas passing through the second hollow space. The use of a single heating element in both the inspiratory tube and the expiratory tube reduces the complexity of the present systems, avoids the need for multiple temperature sensors and temperature controllers, and provides a system which is forgiving of user errors, for example, in hooking up the present systems backwards. Preferably, a temperature sensor is provided which includes a sensing element positioned in or near the outlet of the inspiratory tube to sense the temperature of the gas exiting the first elongate hollow space. This temperature sensor passes temperature sensing signals to a controller to control the amount of heat supplied to the inspiratory and expiratory tubes. The sensing element is preferably positioned to be spaced apart from the heating element, for example, so that the sensing element does not come in direct contact with the heating element. This feature increases the accuracy and reliability of the sensed temperature, and advantageously reduces the system temperature rise after a gas flow shutdown, for example, because of an equipment change and/or other interruption (for example, for a special patient treatment, such as suctioning) or other disturbance. Also, this feature reduces, and preferably minimizes to the extent possible, the time to reach temperature equilibrium after gas flow is restarted.

In another embodiment, the present tubing circuit systems comprise a temperature sensor assembly including a sensing element positioned at or near the outlet of the inspiratory tube to sense the temperature of the gas exiting the first elongate hollow space. In this embodiment, the manifold assembly includes a coupler to couple the inspiratory tube to the first port and the expiratory tube to the second port. The coupler is adapted to fix the position of the sensing element of the temperature sensor, for example, so the temperature sensor monitors the temperature at the same point in the circuit. In addition, the temperature sensor is structured to pass temperature sensing signals through the first elongate hollow space or the second elongate hollow space, for example, to a controller as described above. This feature, by reducing or even eliminating external environmental heat losses from (or gains to) the temperature sensor, increases the reliability of the sensed temperature and the control of the circuit based on this sensed temperature.

These and other aspects and advantages of the present invention will be apparent in the following detailed description and claims, particularly when considered in conjunction with the accompanying drawings in which like parts bear like reference numerals.

BRIEF DESCRIPTION OF THE DRAWINGS

FIG. 1 is a schematic illustration showing a tubing circuit system in accordance with the present invention in use.

FIG. 1a is a schematic illustration showing the expandable character of a portion of the tubing circuit system shown in FIG. 1.

FIG. 2 is a perspective view of the manifold assembly of the tubing circuit system shown in FIG. 1, with the coupler of this manifold assembly broken apart.

FIG. 3 is a perspective view of the humidifier manifold of the tubing circuit system shown in FIG. 1.

FIG. 4 is a perspective view of the expiratory tube outlet and ventilator fitting of the tubing circuit system shown in FIG. 1.

FIG. 5 is a sectional view taken generally along line 5—5 of FIG. 1.

FIG. 6 is a sectional view taken generally along line 6—6 of FIG. 3.

DETAILED DESCRIPTION OF THE INVENTION

FIG. 1 illustrates a tubing circuit system, shown generally at 10, in accordance with the present invention in use delivering humidified respiratory gas to the respiratory system of a patient 12. System 10 includes an inspiratory tube 14, and expiratory tube 16 and a manifold assembly 18. As shown in FIG. 3, inspiratory tube 14 defines a first open hollow space 22 which runs from the inlet 24 to the outlet 26 (FIG. 1) of the inspiratory tube.

As shown in FIG. 4, expiratory tube 16 defines a second open hollow space 28 which runs from the inlet 30 (FIG. 1) to the outlet 32 of the expiratory tube.

A single heating wire loop 34 passes through both the first space 22 and the second space 28. Although loop 34 need not pass through the entire length of both spaces 22 and 28, as shown in the presently illustrated system 10, it is preferred that the loop pass through at least a major portion, that is at least about 50%, or at least about 70% of the length of both of these spaces to avoid water condensation and to satisfactorily control the temperature of the gas in the system. In a particularly useful embodiment, heating wire loop 34 passes through 100% of the length of first open hollow space 22. In system 10, loop 34 begins (and ends) at first connector part 36, passes through first port 38 of humidifier manifold 40 into second port 42 of the humidifier manifold. The inlet 24 of inspiratory tube 14 is coupled to this second port 42, so that the loop 34 passes into and through the first space 22, into the manifold assembly 18, and into and through the second space 28. The ventilator fitting 44, to which expiratory tube 16 is coupled, includes a bar 48 which comes in contact with loop 34 and effectively prevents the loop from passing further into the ventilator fitting toward the ventilator 74.

Heating wire loop 34, which is a conventional electrical wire covered with insulation, is only one embodiment of a single heating element which passes through first space 22 and second space 28. Other constructions are possible. For example, a single insulated heating wire, containing both legs of a loop to form an electrical circuit, can be passed through first space 22 and second space 28. The heating element in both the first space 22 and second space 28 is preferably controlled by a single temperature sensor assembly and temperature controller.

Manifold assembly 18 includes a plug portion 50 and a cup portion 52. Referring to FIG. 1a, plug portion 50 includes tube extensions 54 and 56 to which the outlet 26 of inspiratory tube 14 and the inlet 30 of expiratory tube 16, respectively, are attached. Cup portion 52 includes tube extensions 58 and 60 to which the expandable inspiratory conduit 62 and the expandable expiratory conduit 64, respectively, are attached. The expandable conduits 62 and 64 are coupled to the appropriate ports of patient manifold 66 which includes a tracheal tube 68 that is passed into the respiratory system of the patient 12. A mask or other conventional patient connection assembly can be used in place of tracheal tube 68, as desired.

As shown in FIG. 1a, expandable conduits 62 and 64 are made of expandable tubing and can be placed or positioned in a compressed state or in a partially or fully expanded or extended state, depending on the specific application involved. For example, if no patient warmer or incubator is involved in the application, the expandable conduits are preferably used in the compressed state. This allows temperature control of the humidified respiratory gas at a point relatively close to where the gas enters the patient 12. However, if a warmer or incubator is used, the expandable conduits 62 and 64 are preferably extended so that the assembled plug portion 50/cup portion 52 is away from the warmer or outside the incubator so that the gas temperature being sensed and controlled is not greatly influenced by the warmer or incubator. Different lengths (compressed lengths) of expandable conduits 62 and 64 can be used, as desired, to suit the particular application and patient involved.

Referring to FIG. 2, patient manifold 66 includes a pressure port 67 which is coupled to pressure line 69 to provide pressure signals to ventilator 74 for control and monitoring purposes. A patient temperature port 71 is also provided and is used to monitor the temperature of the gas very close to the point where it is delivered to the patient. Patient temperature port 71 can also be used to provide suctioning and/or other special or desired treatments to the patient, as needed.

When plug portion 50 is appropriated coupled with or fitted into cup portion 52 of manifold assembly 18, a coupler or coupling 55 is formed, and through fluid passages are provided between inspiratory tube 14 and expandable conduit 62, and between expandable conduit 64 and expiratory tube 16. In this manner, humidified respiratory gas from humidifier 70 passes through inspiratory tube 14, expandable tube 62 and patient manifold 66. Exhaled respiratory gas from patient 12 and unused humidified respiratory gas are passed from patient manifold 66, through expandable tube 64 and expiratory tube 16 to ventilator 74. The coupler 55, with the tubes extending therefrom, as described herein, has the general appearance of an H, and therefore manifold assembly 18 can be referred to as a "H-manifold".

Plug portion 50 of H-manifold 18 performs a number of important functions. As can best be seen in FIGS. 2 and 5, the end 76 of plug portion 50 opposite from the tube extensions 54 and 56 includes a pair of wire grooves 78 and 80 which are structured to hold segments 82 and 84 of loop 34, respectively. Thus, when plug portion 50 is coupled with cup portion 52, segments 82 and 84 of loop 34 are held securely in grooves 78 and 80, respectively.

It should be noted that heating wire loop 34 can, if desired extend into expandable conduit 62 and/or expandable conduit 64. However, it is preferred that coupler 55 includes at least one heating element retainer, such as grooves 78 and 80, to hold a portion of the heating element passing through the coupler.

In addition, the end 76 of plug portion 50 includes a number of outwardly extending projections 88 and blocks 90. With reference to FIG. 5, these projections 88 and blocks 90 extend upwardly from wall 92, which is slightly recessed relative to grooves 78 and 80. These projections 88 and blocks 90 are configured and oriented to fixedly secure one end of thermistor assembly 94 in position so that thermistor bead 96 senses the temperature of the gas at or near the outlet of the inspiratory tube 14 and remains out of contact with loop 34, which is held in place in grooves 78 and 80. Moreover, projections 88 and blocks 90 are arranged so as to direct thermistor signal wire 98 into inspiratory tube 14 where it passes through space 22, through third port 110 of humidifier manifold 40 and is secured to first connector part 36. Thermistor assembly 94 is substantially completely internal within system 10. The environment external of system 10, particularly the external environment at or near the patient, where incubators and/or warmers are often present, has little or no effect on the temperature sensed or the signals communicated by the thermistor assembly 94 and does not cause detrimental temperature gains or losses in thermistor signal wire 98.

With reference to FIG. 3 and FIG. 6, a humidifier thermistor assembly 102 is provided in the second port 42 of the humidifier manifold 40 near the inlet 24 of inspiratory tube 14. Thermistor assembly 102 includes a humidifier thermistor bead 104 which is positioned and held in second port 42 of humidifier manifold 40 so as to monitor the temperature of the humidified respiratory gas exiting humidifier 70 and entering inspiratory tube 14. A series of pegs 106 extend within humidifier manifold 40 and are arranged so that humidifier thermistor wire 108 can be secured thereby so that thermistor bead 104 is properly positioned and held. Thermistor wire 108 exits humidifier manifold 40 through third port 110 and is connected to first connector part 36.

First connector part 36 is connected to second connector part 112. Power wires 114, temperature wires 116 and humidifier temperature wires 118 are connected to second connector part 112. Loop 34, thermistor signal wire 98 and thermistor wire 108 are in electrical communication with power wires 114, temperature wires 116 and humidifier temperature wires 118, respectively. Humidifier wires 118 are passed into humidifier base 120 that is equipped with a control system which, based on the temperature signals received from thermistor wire 108, controls the temperature of humidifier 70. Wires 114 and 116 are passed into a temperature/power controller 121 which, based on the temperature signals received from thermistor signal wire 98, controls the power sent to loop 34. A controller useful as temperature/power controller 121 is that sold by Mauna Loa Medical under the trademark Lavapak. Alternately, temperature/power controller 121 can be eliminated by using a humidifier, and in particular a humidifier base, equipped to perform the functions of both humidifier base 120 and temperature/power controller 121. Of course, if such a "multi-function" humidifier base is employed, second connector port 112 and wires 114 and 116 are adapted to communicate with this "multi-functional" humidifier base, rather than with temperature/power controller 121.

Humidifier 70 is conventionally structured to accept an oxygen-air mixture (or other desired respiratory gas) from ventilator 74 through line 122, and water from water bag 124 through line 126. The gas mixture is heated/humidified in humidifier 70 and the humidified respiratory gas is passed through humidifier manifold 40 into inspiratory tube 14. Ventilator 74 is of conventional construction.

Tubing circuit system 10 functions as follows. System 10 is hooked up as shown in FIG. 1. The humidifier temperature controller is set to provide respiratory gas to inspiratory tube 14 having the desired humidity. The power temperature controller in humidifier base 120 is set so that the temperature sensed by thermistor bead 96 is as desired. Ventilator 74 is started and patient manifold 66 is placed in fluid communication with the respiratory system of patient 12.

During normal operation, system 10 functions very effectively to provide respiratory gas, at controlled temperature, to the patient 12. After a period of time, it may become necessary to suction the patient 12, for example, through port 71. The gas flow through the system 10 can be interrupted while this suctioning occurs. However, the humidifier 70 and control systems in humidifier base 120 can continue to function. Because thermistor bead 96 is positioned in relative proximity to, but out of direct contact with, the loop 34 in coupler 55, the temperature in inspiratory tube 14 (first space 22) remains approximately at the desired level. No low temperature or high temperature alarms are indicated. After the suctioning is completed, ventilator 74 is placed back in operation and tubing circuit system 10 again delivers respiratory gas at the desired temperatures and humidity level very shortly thereafter.

System operation after other flow disruptions, for example, because of equipment changes, other treatments for patient 12 and the like, results in similar rapid recovery of system effectiveness.

An additional advantageous feature of system 10 is that the system operates effectively even if it is hooked up backwards, that is so that inspiratory tube 14 functions as expiratory tube 16 and vice versa. This is so because, for example, a single heating wire loop 34 is used in both tubes 14 and 16, and thermistor 96 (even when it is placed in a space which functions as an expiratory space) is still reasonably close to the patient, and therefore, senses the temperature of the gas leaving the patient (which is quite similar to the temperature of the gas entering the patient). Also, the tubing system 10 is disposable, for example, is discarded after use by one patient. The temperature sensor assemblies 94 and 102 are also disposable so that long term deterioration of or damage to such assemblies, for example, caused by repeated handling, sterilization and the like, is eliminated.

In short, the present tubing circuit systems are straight forward in design and construction; safely, effectively and efficiently deliver humidified respiratory gas to a patient without the need for water traps; rapidly recover from gas flow disruptions and interruptions; are conveniently disposable and are forgiving of user or operator errors.

While this invention has been described with respect to various specific examples and embodiments, it is to be understood that the invention is not limited thereto and that it can be variously practiced within the scope of the following claims.

What is claimed:

1. A tubing circuit system for delivering humidified respiratory gas to a human or an animal comprising:

a first tubing segment defining a first elongate hollow space and having an inlet for receiving humidified respiratory gas for passage through said first elongate hollow space toward the human or animal, and an outlet;

a second tubing segment defining a second elongate hollow space which is external and spaced apart from said first elongate hollow space, said second tubing segment having an inlet for receiving exhaled gas from the human or animal and humidified respiratory gas for passage through said second elongate hollow space away from the human or animal, and an outlet adapted to be joined to a ventilator to provide fluid communication between said second elongate hollow space and the ventilator;

a manifold assembly including a first port coupled to said first tubing segment, and a second port coupled to said second tubing segment; and a heating element positioned in said first elongate hollow space and said second elongate hollow space, and being adapted to provide heat to the humidified respiratory gas passing through said first elongate hollow space and to the exhaled gas and humidified respiratory gas passing through said second elongate hollow space.

2. The tubing circuit system of claim 1 wherein said heating element passes through at least a major portion of the length of each of said first elongate hollow space and said second elongate hollow space.

3. The tubing circuit system of claim 1 which further comprises a temperature sensor assembly including a sensing element positioned in or near the outlet of said first tubing segment to sense the temperature of the gas exiting said first elongate hollow space.

4. The tubing circuit system of claim 3 wherein said temperature sensor assembly includes a signal wire positioned in and along the length of said first elongate hollow space or said second elongate hollow space for passing temperature sensing signals from said sensing element.

5. The tubing circuit system of claim 3 wherein said sensing element comprises a thermistor bead.

6. The tubing circuit system of claim 3 wherein said manifold system includes a coupler to couple said first tubing segment to said first port and said second tubing segment to said second port.

7. A tubing circuit system of claim 6 wherein said heating element comprises a heating wire, and said coupler is adapted to fix the positions of a portion of said heating wire and said sensing element so that said heating wire is in proximity to and spaced apart from said sensing element.

8. The tubing circuit system of claim 7 wherein said coupler defines at least one retainer in which a portion of said heating wire is located.

9. The tubing circuit system of claim 3 which further comprises a single connector holding a portion of said heating element and a portion of said temperature sensor assembly.

10. The tubing circuit system of claim 1 which further comprises a humidifier temperature sensor assembly including a sensing element positioned in or near said inlet of said first tubing segment to sense the temperature of the humidified respiratory gas entering said tubing circuit system.

11. The tubing circuit system of claim 10 which further comprises a single connector holding a portion of said heating element and a portion of said humidifier temperature sensor assembly.

12. The tubing circuit system of claim 3 which further comprises a humidifier temperature sensor assembly including a sensing element positioned in or near said inlet of said first tubing segment to sense the temperature of the humidified respiratory gas entering said tubing circuit system.

13. The tubing circuit system of claim 12 which further comprises a single connector holding a portion of heating element, a portion of said temperature sensor assembly and a portion of said humidifier temperature sensor assembly.

14. A tubing circuit system for delivering humidified respiratory gas to a human or an animal comprising:
a first tubing segment having first and second ends and defining a first elongate hollow space and having an inlet located at or near said first end for receiving humidified respiratory gas for passage through said first elongate hollow space toward the human or animal, and an outlet located at or near said second end;
a second tubing segment defining a second elongate hollow space which is external and spaced apart from said first elongate hollow space, said second tubing segment having an inlet for receiving exhaled gas from the human or animal and humidified respiratory gas for passage through said second elongate hollow space away from the human or animal, and an outlet adapted to be joined to a ventilator to provide fluid communication between said second elongate hollow space and the ventilator;
a manifold assembly including a first port coupled to said first tubing segment, and a second port coupled to said second tubing segment, said manifold assembly including a coupler to couple said first tubing segment to said first port and said second tubing segment to said second port; and
a temperature sensor assembly including a sensing element positioned in or near said outlet of said first tubing segment to sense the temperature of the gas exiting said first elongate hollow space, said coupler being adapted to fix the position of said sensing element, said temperature sensor assembly being structured to pass temperature sensing signals through and along the length of said first elongate hollow space or said second elongate hollow space.

15. The tubing circuit system of claim 14 wherein said sensing element comprises a thermistor bead.

16. The tubing circuit system of claim 14 wherein said temperature sensor assembly includes a signal wire positioned in and along the length of said first elongate hollow space for passing temperature sensing signals from said sensing element.

17. The tubing circuit system of claim 14 which further comprises a humidifier temperature sensor assembly including a sensing element positioned in or near said inlet of said first tubing segment to sense the temperature of the humidified respiratory gas entering said tubing circuit system.

18. The tubing circuit system of claim 17 which further comprises a single connector holding a portion of said temperature sensor assembly and a portion of said humidifier temperature sensor assembly.

19. A tubing circuit system for delivering humidified respiratory gas to a human or animal comprising:
a first tubing segment defining a first elongate hollow space and having an inlet for receiving humidified respiratory gas for passage through said first elongate hollow space toward the human or animal, and an outlet;
a second tubing segment defining a second elongate hollow space which is external and spaced apart from said first elongate hollow space, said second tubing segment having an inlet for receiving exhaled gas from the human or animal and humidified respiratory gas for passage through said second elongate hollow space away from the human or animal, and an outlet adapted to be joined to a ventilator to provide fluid communication between said second elongate hollow space and the ventilator;
a temperature sensor assembly including a sensing element positioned in or near the outlet of said first tubing segment to sense the temperature of the gas exiting said first elongate hollow space, said temperature sensor assembly being structured to pass temperature sensing signals through said first elongate hollow space;
a heating element positioned in said first elongate hollow space and said second elongate hollow space, and being adapted to provide heat to the humidified respiratory gas passing through said first elongate hollow space and to the exhaled gas and humidified respiratory gas passing through said second elongate hollow space; and
a manifold assembly including a first port, a second port and a coupler to couple said first tubing segment to said first port and said second tubing segment to said second port and being adapted to fix the positions of a portion of said heating element and said sensing element so that said heating element is in proximity to and spaced apart from said sensing element.

20. A tubing circuit system of claim 19 which further comprises a humidifier temperature sensor assembly including a sensing element positioned in or near said inlet of said first tubing segment to sense the temperature of the humidified respiratory gas entering said tubing circuit system.

* * * * *